United States Patent [19]
Bailey

[11] 3,997,542
[45] Dec. 14, 1976

[54] 1-(HALOGENATED-ACETYL)-1,2,3,4-TETRAHYDRO-6-QUINOLINOLS AND ESTERS THEREOF

[75] Inventor: Denis Mahlon Bailey, East Greenbush, N.Y.

[73] Assignee: Sterling Drug Inc., New York, N.Y.

[22] Filed: June 23, 1975

[21] Appl. No.: 589,195

[52] U.S. Cl. .............................. 260/287 T; 424/258
[51] Int. Cl.² ....................................... C07D 215/08
[58] Field of Search .................. 260/287 T, 287 CE

[56] References Cited

UNITED STATES PATENTS 2,666,058  5/1950  Neher ........................... 260/287 L
3,793,314  2/1974  Nardi et al. .................... 260/287 L

OTHER PUBLICATIONS

Nagarajan, "Indian J. Chem.," 1969, pp. 848, 852–857.
Svensson et al. "Tetrahedron" 29, 1973, p. 1115ff.
March, "Advanced Organic Chemistry," 1968, pp. 319–320.
House, "Modern Synthetic Reactions," pp. 268, 274 (1965).

Primary Examiner—Donald G. Daus
Assistant Examiner—David E. Wheeler
Attorney, Agent, or Firm—Robert K. Bair; B. Woodrow Wyatt

[57] ABSTRACT

Compounds useful as antiamebic agents are 1-($Ac_1$)-5-R-6-($Ac_2$O)-1,2,3,4-tetrahydroquinolines (I), where $Ac_1$ is haloacetyl, dihaloacetyl or trihaloacetyl with halo being chloro or bromo, R is hydrogen, chloro or bromo, and $Ac_2$ is hydrogen, $Ac_1$, alkanoyl having from one to sixteen carbon atoms, benzoyl, 2(or 3)-thenoyl, 2(or 3)-furoyl or N-(lower-alkyl)carbamoyl. Said compounds are prepared: by reacting 1,2,3,4-tetrahydro-6-quinolinol with an acyl halide of the formula $Ac_1$-halogen to produce 1-($Ac_1$)-1,2,3,4-tetrahydro-6-quinolinol having formula I where R and $Ac_2$ are each hydrogen, $Ac_1$ is defined as in formula I and halide is chloride or bromide; by reacting said 1-($Ac_1$)-1,2,3,4-tetrahydro-6-quinolinol with a chlorinating or brominating agent to produce the corresponding 1-($Ac_1$)-5-chloro(or bromo)-1,2,3,4-tetrahydro-6-quinolinol where $Ac_1$ is defined as in claim 1; and, by reacting 1-($Ac_1$)-5-R-1,2,3,4-tetrahydro-6-quinolinol with an acylating agent providing $Ac_2$ to produce 1-($Ac_1$)-5-R-1,2,3,4-tetrahydro-6-($Ac_2$O)quinoline having formula I where R is hydrogen, chloro or bromo, $Ac_1$ is defined as in formula I and $Ac_2$ is other than hydrogen as defined in formula I.

11 Claims, No Drawings

1-(HALOGENATED-ACETYL)-1,2,3,4-TETRAHYDRO-6-QUINOLINOLS AND ESTERS THEREOF

BACKGROUND OF THE INVENTION

1. Field of the Invention

This invention relates to 1-acyl-1,2,3,4-tetrahydro-6-quinolinols useful as antiamebic agents and to their preparation.

2. Description of the Prior Art 1,2,3,4-Tetrahydro-6-quinolinol and its unidentified acetyl derivative are disclosed in the German Patent 42,187 [March 5, 1877; Frdl. 1, 181 (1877–1887); Beil. 21, 61 (1935)].

1-Acetyl-1,2,3,4-tetrahydro-6-quinolinol and its bromination to yield 1-acetyl-5-bromo-1,2,3,4-tetrahydro-6-quinolinol are shown by Svensson et al. [Tetrahedron 29, 1115 (1973)].

1-Benzoyl-1,2,3,4-tetrahydro-6-quinolinol and 6-acetoxy-1-benzoyl-1,2,3,4-tetrahydroquinoline are shown by Miyaki et al. [J. Pharm. Soc. Japan 59, 222–4 (1939); C.A. 34, 7910[8] (1940)].

1-(Chloroacetyl)-1,2,3,4-tetrahydro-8-methylquinoline is shown by Sugimoto [J. Pharm. Soc. Japan 64, No. 7A, 15–19 (1944); C.A. 46, 114d (1952)].

There is no mention in the above-noted references of any pharmaceutical utility for the compounds disclosed therein.

SUMMARY OF THE INVENTION

In its composition aspect, the invention relates to certain 1-(halogenated-acetyl)-1,2,3,4-tetrahydro-6-quinolinols and esters thereof, and processes for their preparation. These compounds are useful as antiamebic agents.

The invention in its process aspects comprises reacting 1,2,3,4-tetrahydro-6-quinolinol with an halogentated-acetyl halide of the formula $Ac_1$-halogen to produce 1($Ac_1$)-1,2,3,4-tetrahydro-6-quinolinol, reacting said 1-($Ac_1$)-1,2,3,4-tetrahydro-6-quinolinol with a chlorinating or brominating agent to produce the corresponding 1-($Ac_1$)-5-chloro(or bromo)-1,2,3,4-tetrahydro-6-quinolinol; and, reacting 1-($Ac_1$)-5-R-1,2,3,4-tetrahydro-6-quinolinol, where R is hydrogen, chloro or bromo, with an acylating agent providing $Ac_2$ to produce 1-($Ac_1$)-5-R-1,2,3,4-tetrahydro-6-($Ac_2$O)-quinoline where $Ac_2$ is $Ac_1$, alkanoyl having from one to sixteen carbon atoms, benzoyl, 2(or 3)-thenoyl, 2(or 3)-furoyl or N-(lower-alkyl)carbamoyl.

DETAILED DESCRIPTION INCLUSIVE OF PREFERRED EMBODIMENTS

The invention in its composition aspect resides in the compounds having formula I

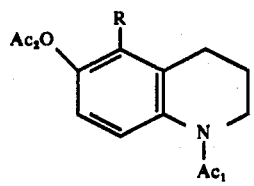

I where $Ac_1$ is haloacetyl, dihaloacetyl or trihaloacetyl with halo being chloro or bromo, R is hydrogen, chloro or bromo, and $Ac_2$ is hydrogen, $Ac_1$, alkanoyl having from one to sixteen carbon atoms, benzoyl, 2(or 3)-thenoyl, 2(or 3)-furoyl or N-(lower-alkyl)carbamoyl. The compounds of formula I are useful as intestinal antiamebic agents, as determined by standard chemotherapeutic evaluation procedures in vivo in hamsters. Preferred embodiments because of high antiamebic activity and low cost of preparation are the compounds of formula I where $Ac_1$ is dichloroacetyl and R is hydrogen or chloro. Particularly preferred compounds are those having formula I where $Ac_1$ is dichloroacetyl, R is hydrogen or chloro and $Ac_2$ is hydrogen, benzoyl, 2-thenoyl or 2-furoyl.

The invention in a process aspect for preparing the compounds of formula I comprises reacting 1,2,3,4-tetrahydro-6-quinolinol with an acyl halide of the formula $Ac_1$-halogen to produce 1-($Ac_1$)-1,2,3,4-tetrahydro-6-quinolinol having formula I where R and $Ac_2$ are each hydrogen, $Ac_1$ is defined as in formula I and halide is chloride or bromide. The invention in another process aspect comprises reacting said 1-($Ac_1$)-1,2,3,4-tetrahydro-6-quinolinol with a chlorinating or brominating agent to produce the corresponding 1-($Ac_1$)-5-chloro(or bromo)-1,2,3,4-tetrahydro-6-quinolinol which is then reacted with an acylating agent providing $Ac_2$ to produce the 1-($Ac_1$)-1,2,3,4-tetrahydro-5-chloro(or bromo)-6-($Ac_2$O)-quinoline having formula I where $Ac_2$ is other than hydrogen as defined in formula 1. In another process aspect of the invention, the 1-($Ac_1$)-1,2,3,4-tetrahydro-6-quinolinol is reacted with an acylating agent providing $Ac_2$ to produce 1-($Ac_1$)-1,2,3,4-tetrahydro-6-($Ac_2$O)quinoline having formula I where R is hydrogen and $Ac_2$ is other than hydrogen as defined in formula 1. Other process aspects of the invention consists of the combinations of two or more of the said process aspects of the invention, said combinations defined hereinbelow in the claims.

The term "lower-alkyl" as used herein, e.g., in "N-(lower-alkyl)carbamoyl" as one of the meanings for $Ac_2$, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The molecular structures of the composition aspect (I) of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows;

The N-acylation reaction which comprises reacting 1,2,3,4-tetrahydro-6-hydroxyquinoline with an acyl halide of the formula $Ac_1$-halogen to produce 1-($Ac_1$)-1,2,3,4-tetrahydro-6-hydroxyquinoline having formula I, where R and $Ac_2$ are each hydrogen, $Ac_1$ is defined as in formula I and halide is chloride or bromide, is carried out by heating the reactants in the range of 35°–115° C, preferably about 50°–80° C., in a suitable water-immiscible organic solvent inert under the reaction conditions, e.g., chloroform, ethylene dichloride, methylene dichloride, carbon tetrachloride, benzene, ether, toluene and the like, in the absence or presence of an acid-acceptor, e.g., a lower-aliphatic amine such as triethylamine, an alkali or alkaline earth carbonate or bicarbonate such as sodium carbonate, calcium carbonate, potassium bicarbonate, and the like.

The O-acylation reaction which comprises reacting 1-($Ac_1$)-1,2,3,4-tetrahydro-6-quinolinol or 1-($Ac_1$)-5-chloro(or bromo)-1,2,3,4-tetrahydro-6-quinolinol with an acylating agent providing $Ac_2$ to produce the corresponding 6-($Ac_2$O)quinoline having formula 1, where $Ac_2$ is other than hydrogen, is carried out preferably by carefully mixing the reactants with cooling (to about 0°–10° C.) and stirring in a suitable solvent in the presence of an acid-acceptor, said solvent and acid-acceptor such as those given above for the N-acylation.

The reaction which comprises reacting 1-($Ac_1$)-1,2,3,4-tetrahydro-6-quinolinol with a chlorinating or brominating agent to yield the corresponding 1-($Ac_1$)-5-chloro(or bromo)-1,2,3,4-tetrahydro-6-quinolinol is carried out in an inert solvent such as noted above for the N-acylation by mixing the reactants in the presence or absnece of an acid-acceptor such as noted above. The chlorination is conveniently run by mixing the 1-($Ac_1$)-1,2,3,4-tetrahydro-6-quinolinol in said solvent, e.g., benzene, with sulfuryl chloride (as a source of chlorine) whereupon an exothermic reaction ensues. Alternatively, gaseous chlorine can be bubbled into a hot benzene solution of the 1-($Ac_1$)-1,2,3,4-tetrahydro-6-quinolinol. Completion of the reaction is indicated by cessation of HCl evolution or by TLC examination. Completion of the bromination reaction is indicated by disappearance of the bromine color from the reaction mixture.

The following examples will further illustrate the invention without, however, limiting it thereto.

A. 1-($Ac_1$)-1,2,3,4-Tetrahydro-6-quinolinols and Esters

A-1. 1-(Dichloroacetyl)-1,2,3,4-tetrahydro-6-quinolinol — To a stirred mixture containing 14.9 g. of 1,2,3,4-tetrahydro-6-quinolinol and 250 ml. of dry ethylene dichloride was added dropwise 16.2 g. of dichloroacetyl chloride and the resulting reaction mixture was stirred on a steam bath for fourteen hours. The reaction mixture was heated in vacuo to remove the ethylene dichloride. The remaining material was taken up in chloroform and the chloroform removed in vacuo to yield 28 g. of powder. The powder was slurried at room temperature with 100 ml. of n-hexane containing 10 ml. of isopropyl alcohol and the remaining solid, 24.5 g., was recrystallized twice from chloroform-n-hexane and dried at 60° C. and 0.1 mm. for seven hours to yield 10.5 g. of 1-(dichloroacetyl)-1,2,3,4-tetrahydro-6-quinolinol, m.p. 136°–136.5° C.

A-2. 1-(Dichloroacetyl)-6-(2-furoyloxy)-1,2,3,4-tetrahydroquinoline — An 11.0 g. portion of 1-(dichloroacetyl)-1,2,3,4-tetrahydro-6-quinolinol was dissolved by heating with about 200 ml. of chloroform. The resulting clear, dark solution was chilled in an ice bath and to it was added with stirring 6.3 ml. of triethylamine followed by 5.8 g. of 2-furoyl chloride in 15 ml. of chloroform. The reaction mixture was then stirred for one hour, the ice bath removed and stirring continued for another three hours. The cold reaction mixture was poured into a separatory funnel containing a cold mixture of 4 ml. of acetic acid plus ice and water. The mixture was then allowed to warm-up to room temperature and washed successively twice with water, twice with aqueous sodium bicarbonate solution and twice with water. The resulting mixture was treated with decolorizing charcoal and dried over anhydrous sodium sulfate, and filtered. The filtrate was heated in vacuo to remove most of the chloroform. A few ml. of methanol was added to destroy any unreacted acyl chloride. The solid that separated was colleced and recrystallized once from methanol and once from ethyl acetate to yield 13.1 g. of 1-(dichloroacetyl)-6-(2-furoyloxy)-1,2,3,4-tetrahydroquinoline, m.p. 150.5°–151° C., after drying for twenty-four hours at 80° C. at 200 mm.

A-3. 1-(Dichloroacetyl)-1,2,3,4-tetrahydro-6-(2-thenoyloxy)quinoline, m.p. 109°–110.5° C., 8.4 g., was prepared following the procedure described in Example A-2 using 7.0 g. of 1-(dichloroacetyl)-1,2,3,4-tetrahydro-6-quinolinol, 140 ml. of chloroform, 4.2 ml. of triethylamine, 4.3 g. of 2-thenoyl chloride, two recrystallizations from isproyl alcohol and drying at 60° C. and 200 mm. for 18 hours.

A-4. 6-Benzoyloxy-1-(dichloroacetyl)-1,2,3,4-tetrahydroquinoline — A 9.1 g. portion of 1-(dichloroacetyl)-1,2,3,4-tetrahydro-6-quinolinol was dissolved in 150 ml. of warm chloroform. To the chloroform solution at room temperature was added 5.6 ml. of triethylamine and the resulting solution was cooled in an ice bath to 0°–5° C. To the chilled solution was added dropwise with stirring 4.3 ml. of benzoyl chloride and the resulting reaction mixture was stirred for one hour in the ice bath. To the reaction mixture was added 7 ml. of glacial acetic acid and the resulting reaction mixture was washed twice with cold water, once with sodium bicarbonate solution, and then dried over anhydrous sodium sulfate and filtered. The filtrate was heated in vacuo to remove the solvent and the remaining material was allowed to stand at room temperature whereupon ti solidified. This material was slurried with isopropyl alcohol and the solid was collected and recrystallized from isopropyl alcohol to yield 10.5 g. of 6-benzoyloxy-1-(dichloroacetyl)-1,2,3,4-tetrahydroquinoline, m.p. 119°–119.5° C.

A-5. 6-(n-Butanoyloxy)-1-(dichloroacetyl)-1,2,3,4-tetrahydroquinoline, m.p. 107°–108° C., 12 g., was prepared following the procedure described in Example A-4 using 11.8 g. of 1-(dichloroacetyl)-1,2,3,4-tetrahydro-6-quinolinol, 200 ml. of chloroform, 6.7 ml. of triethylamine, 5.1 g. of n-butanoyl chloride in chloroform, slurrying the residue after removal of the chloroform from the reaction mixture with hot n-hexane and a small quantity of isopropyl alcohol, and two recrystallizations from isopropyl alcohol plus drying at 70° C. and 200 mm. for four hours.

A-6. 1-(Dichloroacetyl)-6-(n-hexadecanoyloxy)-1,2,3,4-tetrahydroquinoline — A mixture containing 7.0 g. of 1-(dichloroacetyl)-1,2,3,4-tetrahydro-6-quinolinol in 75 ml. of chloroform, 2.7 g. of triethylamine and 8.2 g. of palmitoyl chloride was refluxed for two hours and thirty-five minutes and then allowed to stand at room temperature over the weekend. The reaction mixture was washed successively with 1N aqueous hydrochloric acid and saturated aqueous sodium bicarbonate solution, dried over anhydrous sodium sulfate and filtered. The filtrate was heated in vacuo to remove the chloroform. The residue was combined with another 3.0 g. of material obtained from another run of the same reaction and the combined material was recrystallized from ethanol to yield 11.3 g. of 1-(dichlorπacetyl)-6-(n-hexadecanoyloxy)-1,2,3,4-tetrahydroquinoline, m.p. 84°–86° C.

A-7. 1-(Dichloroacetyl)-1,2,3,4-tetrahydro-6-(N-methylcarbamoyloxy)quinoline — A mixture containing 7.0 g. of 1-(dichloroacetyl)-1,2,3,4-tetrahydro-6-quinolinol suspended in 280 ml. of benzene, 4.2 g. of methyl isocyanate and 14 drops of triethylamine was stirred at ambient temperature, about 25°–30° C., for 90 minutes. The reaction mixture was heated in vacuo to remove the volatile materials and the residue was scratched to induce crystallization. The resulting solid was dissolved in 100 ml. of hot toluene, the hot solution treated with decolorizing charcoal and filtered, and the filtrate cooled, finally to 5° C. The resulting precipitate was collected and washed with 20 ml. of toluene and dried in vacuo at 40° C. and 50 mm. to yield 6 g. of 1-(dichloroacetyl)-1,2,3,4-tetrahydro-6-(N-methylcarbamoyloxy)quinoline, m.p. 1130°–117° C.

A-8. 1-Chloroacetyl)-1,2,3,4-tetrahydro-6-quinolinol — A stirred mixture containing 15.0 g. of 1,2,3,4-tetrahydro-6-quinolinol in 250 ml. of dry chloroform, 7.5 g. of sodium carbonate and 12.5 g. of chloroacetyl chloride was refluxed for about sixteen hours and filtered while hot. The collected solids were recrystallized from acetonitrile to yield 14.9 g. of 1-(chloroacetyl)-1,2,3,4-tetrahydro-6-quinolinol, m.p. 146.5°–150° C.

A-9. 1,2,3,4-Tetrahydro-1-(trichloroacetyl)-6-quinolinol — A stirred mixture containing 15.0 g. of 1,2,3,4-tetrahydro-6-quinolinol in 250 ml. of dry chloroform, 10.0 g. of calcium carbonate and 18.0 g. of trichloroacetyl chloride was refluxed for about 24 hours. To the reaction mixture was added another 9 g. (5 ml.) of trichloroacetyl chloride and the mixture was refluxed with stirring for an additional three hours, allowed to cool to room temperature and then poured into 200 ml. of water. The mixture was brought to a pH of about 7 with solid sodium bicarbonate. The chloroform layer was separated and the aqueous layer was extracted with three 400 ml. portions of benzene. The benzene extracts and the chloroform layer were combined and washed with 5% aqueous sodium bicarbonate until the wash water remained basic. The benzene-chloroform solution was dried over anhydrous sodium sulfate and the solvents removed in vacuo. The remaining residue was recrystallized twice from methylene dichloride, the second time using decolorizing charcoal, and the resulting product was dried at 40° C. and 50 mm. to yield 9.25 g. of 1,2,3,4-tetrahydro-1-(trichloroacetyl)-6-quinolinol, m.p. 153°–155° C.

Following the procedure described in Example A-1 but using in place of dichloroacetyl chloride a molar equivalent quantity of the appropriate acylating agent, i.e., $Ac_1$-halogen, the 1-acyl-1,2,3,4-tetrahydro-6-quinolinols of Examples A-10 thru A-13 are obtained:

A-10. 1-(Dibromoacetyl)-1,2,3,4-tetrahydro-6-quinolinol using dibromoacetyl bromide.

A-11. 1-(bromoacetyl)-1,2,3,4-tetrahydro-6-quinolinol using bromoacetyl bromide.

A-12. 1-(Tribromoacetyl)-1,2,3,4-tetrahydro-6-quinolinol using tribromoacetyl chloride.

A-13. 1-(Bromochloroacetyl)-1,2,3,4-tetrahydro-6-quinolinol using bromochloroacetyl chloride.

Following the procedure described in Example A-2 but using in place of 2-furoyl chloride and 1-(dichloroacetyl)-1,2,3,4-tetrahydro-6-quinolinol molar equivalent quantities respectively of the appropriate acylating agent and 1-($Ac_1$)-1,2,3,4-tetrahydro-6-quinolinol, the compounds of Examples A-14 thru A-26 are obtained:

A-14. 1-(Dichloroacetyl)-6-formyloxy-1,2,3,4-tetrahydroquinoline using 1-(dichloroacetyl)-1,2,3,4-tetrahydro-6-quinolinol and acetic-formic anhydride.

A-15. 6-Acetoxy-1-(dichloroacetyl)-1,2,3,4-tetrahydroquinoline using 1-(dichloroacetyl)-1,2,3,4-tetrahydro-6-quinolinol and acetyl chloride.

A-16. 6-(2-Furoyloxy)-1-(trichloroacetyl)-1,2,3,4-tetrahydroquinoline using 1-(trichloroacetyl)-1,2,3,4-tetrahydro-6-quinolinol and 2-furoyl chloride.

A-17. 6-(2-Thenoyloxy)-1-(trichloroacetyl)-1,2,3,4-tetrahydroquinoline using 1-(trichloroacetyl)-1,2,3,4-tetrahydro-6-quinolinol and 2-thenoyl chloride A-18. 1-(Chloroacetyl)-6-(2-thenoyloxy)-1,2,3,4-tetrahydroquinoline using 1-(chloroacetyl)-1,2,3,4-tetrahydro-6-quinolinol and 2-thenoyl chloride.

A-19. 1-(Chloroacetyl)-6-(2-furoyloxy)-1,2,3,4-tetrahydroquinoline using 1-(chloroacetyl)-1,2,3,4-tetrahydro-6-quinolinol and 2-furoyl chloride.

A-20. 1-(Bromoacetyl)-6-(2-furoyloxy)-1,2,3,4-tetrahydroquinoline using 1-(bromoacetyl)-1,2,3,4-tetrahydro-6-quinolinol and 2-furoyl chloride.

A-21. 1-(Dibromoacetyl)-6-(2-furoyloxy)-1,2,3,4-tetrahydroquinoline using 1-(dibromoacetyl)-1,2,3,4-tetrahydro-6-quinolinol and 2-furoyl chloride.

A-22. 1-(Dibromoacetyl)-6-(2-thenoyloxy)-1,2,3,4-tetrahydroquinoline using 1-(dibromoacetyl)-1,2,3,4-tetrahydro-6-quinolinol and 2-thenoyl chloride.

A-23. 1-(Tribromoacetyl)-6-(2-thenoyloxy)-1,2,3,4-tetrahydroquinoline using 1-(tribromoacetyl)-1,2,3,4-tetrahydro-6-quinolinol and 2-thenoyl chloride.

A-24. 1-(Tribromoacetyl)-6-(2-furoyloxy)-1,2,3,4-tetrahydroquinoline using 1-(tribromoacetyl)-1,2,3,4-tetrahydro-6-quinolinol and 2-furoyl chloride.

A-25. 1-(Dichloroacetyl)-6-(3-furoyloxy)-1,2,3,4-tetrahydroquinoline using 1-(dichloroacetyl)-1,2,3,4-tetrahydro-6-quinolinol and 3-furoyl chloride.

A-26. 1-(Dichloroacetyl)-6-(3-thenoyloxy)-1,2,3,4-tetrahydroquinoline using 1-(dichloroacetyl)-1,2,3,4-tetrahydro-6-quinolinol and 3-thenoyl chloride.

Following the procedure described in Example A-7 but using in place of methyl isocyanate a molar equivalent quantity of the appropriate lower-alkyl isocyanate, the compounds of A-27 and A-28 are obtained:

A-27. 1-(Dichloroacetyl)-6-(N-ethylcarbamoyloxy)-1,2,3,4-tetrahydroquinoline using methyl isocyanate.

A-28. 1-(Dichloroacetyl)-6-(N-n-hexylcarbamoyloxy)-1,2,3,4-tetrahydroquinoline using n-hexyl isocyanate.

Following the procedure described in Example A-2 but using in place of 2-furoyl chloride a molar equivalent quantity of the corresponding acyl halide, the compounds of Examples A-29 thru A-33 are obtained:

A-29. 6-(Chloroacetoxy)-1-(dichloroacetyl)-1,2,3,4-tetrahydroquinoline using chloroacetyl chloride.

A-30. 1-(Dichloroacetyl)-6-formyloxy-1,2,3,4-tetrahydroquinoline using acetic-formic anhydride.

A-31. 1-(Dichloroacetyl)-6-(trichloroacetoxy)-1,2,3,4-tetrahydroquinoline using trichloroacetyl chloride.

A-32. 6-(Dibromoacetoxy)-1-(dichloroacetyl)-1,2,3,4-tetrahydroquinoline using dibromoacetyl chloride.

A-33. 6-(Dichloroacetoxy)-1-(dichloroacetyl)-1,2,3,4-tetrahydroquinoline using dichloroacetyl chloride.

B. 1-($Ac_1$)-5-Chloro(or bromo)-1,2,3,4-tetrahydro-6-quinolinols and Esters

B-1. 5-Chloro-1-(dichloroacetyl)-1,2,3,4-tetrahydro-6-quinolinol — To a stirred solution of 32 g. of 1-(dichloroacetyl)-1,2,3,4-tetrahydro-6-quinolinol in 400 ml. of hot benzene was added rapidly with stirring 17.7 g. of sulfuryl chloride whereupon the reaction mixture refluxed spontaneously. After refluxing subsided, the reaction mixture was refluxed for another one hour and filtered while hot to collect 21.8 g. of the product, m.p. 189°–191.5° C. This product, 5-chloro-1-(dichloroacetyl)-1,2,3,4-tetrahydro-6-quinolinol was recrystallized from acetonitrile to yield 19.4 g. of the product, m.p. 189.5°–192.5° C.

B-2. 5-Bromo-1-(dichloroacetyl)-1,2,3,4-tetrahydro-6-quinolinol — To a stirred mixture containing 6.15 g. of 1-(dichloroacetyl)-1,2,3,4-tetrahydro-6-quinolinol in 100 ml. of chloroform and 2.0 g. of calcium carbonate at −5° C. was added over a fifty-five minute period with stirring a solution containing 4.0 g. of bromine in 50 ml. of chloroform. The resulting reaction mixture was stirred at −5 to 0° C. for about ninety minutes until all of the bromine color was gone from the reaction mixture. There was then added about 600 ml. of chloroform and the resulting mixture was washed twice with 10% aqueous sodium bicarbonate solution and once with water The chloroform solution was dried over anhydrous sodium sulfate and the chloroform removed in vacuo. The remaining material was crystallized from acetonitrile and then recrystallized from the same solvent to yield 2.3 g. of 5-bromo-1-(dichloroacetyl)-1,2,3,4-tetrahydro-6-quinolinol, m.p. 207°–210° C.

B-3. 5-Chloro-1-(dichloroacetyl)-6-(2-furoyloxy)-1,2,3,4-tetrahydroquinoline — A solution of 15.74 g. of 5-chloro-1-(dichloroacetyl)-1,2,3,4-tetrahydro-6-quinolinol and 7.4 ml. of triethylamine in 500 ml. of chloroform was cooled in an ice bath and 7.15 g. of 2-furoyl chloride was added with stirring. The resulting reaction mixture was removed from the bath and stirred for two hours. The reaction mixture was washed with 200 ml. of 0.5N hydrochloric acid and the hydrochloric acid wash was extracted with 50 ml. of chloroform. The chloroform wash and reaction mixture were combined and washed successively with 50 ml. of 5% aqueous sodium bicarbonate solution and 50 ml. of water, dried over anhydrous sodium sulfate and filtered. The chloroform was removed in vacuo to yield a yellow oily material which crystallized when scratched. The crystalline material was recrystallized from ethanol and dried at 40° C. and 50 mm. to yield 17 g. of 5-chloro-1-(dichloroacetyl)-6-(2-furoyloxy)-1,2,3,4-tetrahydroquinoline, m.p. 132°–133° C.

B-4. 5-Bromo-1-(dichloroacetyl)-6-(2-furoyloxy)-1,2,3,4-tetrahydroquinoline, m.p. 159°–162° C., 5.8 g., was prepared following the procedure described in Example B-3 using 5.68 g. of 5-bromo-1-(dichloroacetyl)-1,2,3,4-tetrahydro-6-quinolinol in 200 ml. of chloroform, 1.73 g. of triethylamine, 2.24 g. of 2-furoyl chloride in 15 ml. of chloroform and a reaction period of four hours.

B-5. 5-Chloro-1-(dichloroacetyl)-1,2,3,4-tetrahydro-6-(2-thenoyloxy)quinoline — A 5.0 g. portion of 5-chloro-1-(dichloroacetyl)-1,2,3,4-tetrahydro-6-quinolinol was dissolved in 160 ml. of hot chloroform, 1.2 g. of triethylamine was added and the solution was cooled to 0° C. To the stirred solution was added 2.55 g. of 2-thenoyl chloride, the reaction mixture was removed from the ice bath and allowed to warm up to room temperature and stirring was continued for about three hours. The reaction mixture was washed successively with two 150 ml. portions of 5% aqueous sodium bicarbonate solution, once with 200 ml. of 1.5N hydrochloric acid, and once with 200 ml. of water. The washed reaction mixture was dried over anhydrous sodium sulfate, filtered and the filtrate evaporated in vacuo to yield an oily residue which solidified when triturated. The solid was then recrystallized from ethanol and dried for about 15 hours at 60° C. at 50 mm. to yield 5.2 q. of 6-chloro-1-(dichloroacetyl)-1,2,3,4-tetrahydro-6-(2-thenoyloxy)quinoline, m.p. 131°–134° C.

B-6. 5-Bromo-1-(dichloroacetyl)-1,2,3,4-tetrahydro-6-(2-thenoyloxy)quinoline, m.p. 149°–150° C., 2.05 g., was prepared following the procedure described in Example B-5 using 2.6 g. of 5-bromo-1-(dichloroacetyl)-1,2,3,4-tetrahydro-6-quinolinol in 80 ml. of chloroform, 0.79 g. of triethylamine, and 1.16 g. of 2-thenoyl chloride.

Following the procedure described in Example B-3 but using in place of 2-furoyl chloride a molar equivalent quantity of the appropriate acylating agent, the compounds of Examples B-7 thru B-9 are obtained:

B-7. 6-Benzoyloxy-5-chloro-1-(dichloroacetyl)-1,2,3,4-tetrahydroquinoline using benzoyl chloride.

B-8. 5-Chloro-1-(dichloroacetyl)-6-formyloxy-1,2,3,4-tetrahydroquinoline using acetic-formic anhydride.

B-9. 6-Acetoxy-5-chloro-1-(dichloroacetyl)-1,2,3,4-tetrahydroquinoline using acetyl chloride.

Following the procedure described in Examples B-1 but using in place of 1-(dichloroacetyl)-1,2,3,4-tetrahydro-6-quinolinol a molar equivalent quantity of the appropriate 1-(Ac$_1$)-1,2,3,4-tetrahydro-6-quinolinol, the compounds of Examples B-10 thru B-12 are obtained:

B-10. 5-Chloro-1-(chloroacetyl)-1,2,3,4-tetrahydro-6-quinolinol using 1-(chloroacetyl)-1,2,3,4-tetrahydro-6-quinolinol.

B-11. 5-Chloro-1-(trichloroacetyl)-1,2,3,4-tetrahydro-6-quinolinol using 1-(trichloroacetyl)-1,2,3,4-tetrahydro-6-quinolinol.

B-12. 5-Chloro-1-(dibromoacetyl)-1,2,3,4-tetrahydro-6-quinolinol using 1-(dibromoacetyl)-1,2,3,4-tetrahydro-6-quinolinol.

Following the procedure described in Example B-2 but using in place of 1-(dichloroacetyl)-1,2,3,4-tetrahydro-6-quinolinol a molar equivalent quantity of the appropriate 1-(Ac$_1$)-1,2,3,4-tetrahydro-6-quinolinol, the compounds of Examples B-13 and B-14 are obtained:

B-13. 5-Bromo-1-(dibromoacetyl)-1,2,3,4-tetrahydro-6-quinolinol using 1-(dibromoacetyl)-1,2,3,4-tetrahydro-6-quinolinol.

B-14. 5-Bromo-1-(tribromoacetyl)-1,2,3,4-tetrahydro-6-quinolinol using 1-(tribromoacetyl)-1,2,3,4-tetrahydro-6-quinolinol.

Following the procedure described in Example B-3 but using in place of 2-furoyl chloride a molar equivalent quantity of the appropriate acylating agent and in place of 5-chloro-1-(dichloroacetyl)-1,2,3,4-tetrahydro-6-quinolinol a molar equivalent quantity of the appropriate 5-halo-1-(Ac$_1$)-1,2,3,4-tetrahydro-6-quinolinol, the compounds of Examples B-15 thru B-22 are obtained:

B-15. 5-Chloro-1-(chloroacetyl)-6-(2-furoyloxy)-1,2,3,4-tetrahydroquinoline using 5-chloro-1-(chloroacetyl)-1,2,3,4-tetrahydro-6-quinolinol and 2-furoyl chloride.

B-16. 5-Chloro-1-(chloroacetyl)-6-(2-thenoyloxy)-1,2,3,4-tetrahydroquinoline using 5-chloro-1-(chloroacetyl)-1,2,3,4-tetrahydro-6-quinolinol and 2-thenoyl chloride.

B-17. 5-Bromo-1-(dibromoacetyl)-6-(2-thenoyloxy)-1,2,3,4-tetrahydrodquinoline using 5-bromo-1-(dibromoacetyl)-1,2,3,4-tetrahydro-6-quinolinol and 2-thenoyl chloride.

B-18. 5-Bromo-1-(dibromoacetyl)-6-(2-furoyloxy)-1,2,3,4-tetrahydroquinoline using 5-bromo-1-(dibromoacetyl)-1,2,3,4-tetrahydro-6-quinolinol and 2-furoyl chloride.

B-19. 5-Chloro-1-(chloroacetyl)-6-(2-furoyloxy)-1,2,3,4-tetrahydroquinoline using 5-chloro-1-(chloroacetyl)-1,2,3,4-tetrahydro-6-quinolinol and 2-furoyl chloride.

B-20. 5-Chloro-1-(chloroacetyl)-6-(2-thenoyloxy)-1,2,3,4-tetrahydroquinoline using 5-chloro-1-(chloroacetyl)-1,2,3,4-tetrahydro-6-quinolinol and 2-thenoyl chloride.

B-21. 5-Chloro-1-(trichloroacetyl)-6-(2-thenoyloxy)-1,2,3,4-tetrahydroquinoline using 5-chloro-1-(trichloroacetyl)-1,2,3,4-tetrahydro-6-quinolinol and 2-thenoyl chloride.

B-22. 5-Chloro-1-(trichloroacetyl)-6-(2-furoyloxy)-1,2,3,4-tetrahydroquinoline using 5-chloro-1-(trichloroacetyl)-1,2,3,4-tetrahydro-6-quinolinol and 2-furoyl chloride.

B-23. 5-Chloro-1-(dichloroacetyl)-6-(3-thenoyloxy)-1,2,3,4-tetrahydroquinoline using 5-chloro-1-(dichloroacetyl)-1,2,3,4-tetrahydro-6-quinolinol and 3-thenoyl chloride.

B-24. 5-Chloro-1-(dichloroacetyl)-6-(3-furoyloxy)-1,2,3,4-tetrahydroquinoline using 5-chloro-1-(dichloroacetyl)-1,2,3,4-tetrahydro-6-quinolinol and 3-furoyl chloride.

Following the procedure described in Example A-7 but using in place of 1-(dichloroacetyl)-1,2,3,4-tetrahydro-6-quinolinol a molar equivalent quantity of 5-chloro-1-(dichloroacetyl)-1,2,3,4-tetrahydro-6-quinolinol and in place of methyl isocyanate a molar equivalent quantity of the appropriate lower-alkyl isocyanate, the compounds of Examples B-25 and B-26 are obtained:

B-25. 5-Chloro-1-(dichloroacetyl)-1,2,3,4-tetrahydro-6-(N-ethylcarbamoyloxy)quinoline using ethyl isocyanate.

B-26. 5-Chloro-1-(dichloroacetyl)-1,2,3,4-tetrahydro-6-(N-n-hexylcarbamoyloxy)quinoline using n-hexyl isocyanate.

B-27. 5-Chloro-1-(dichloroacetyl)-1,2,3,4-tetrahydro-6-(N-methylcarbamoyloxy)quinoline is obtained following the procedure described in Example A-7 but using in place of 1-(dichloroacetyl)-1,2,3,4-tetrahydro-6-quinolinol a molar equivalent quantity of 5-chloro-1(dichloroacetyl)-1,2,3,4-tetrahydro-6-quinolinol.

Following the procedure described in Example B-3 but using in place of 2-furoyl chloride a molar equivalent quantity of the appropriate acylating agent, the compounds of Examples B-28 and B-29 are obtained:

B-28. 5-Chloro-6-(dichloroacetoxy)-1-(dichloroacetyl)-1,2,3,4-tetrahydroquinoline using dichloroacetyl chloride.

B-29. 5-Chloro-1-(dichloroacetyl)-6-(trichloroacetoxy)-1,2,3,4tetrahydroquinoline using trichloroacetyl chloride.

The 1-($Ac_1$)-5-R-6-($Ac_2O$)-1,2,3,4-tetrahydroquinolines of formula I have intestinal amebicidal activity, as determined by standard chemotherapeutic test procedures in hamsters infected with *Endamoeba criceti*. These compounds when administered orally in 10% gelatin suspension to hamsters infected with *E. criceti* were found to completely clear the animals of the infection at varying dose levels of compounds per kg. of body weight per day for three consecutive days. Many of the compounds have $ED_{50}$ values below 10 mg./kg.day × 3 days, $ED_{50}$ meaning the effective dose necessary to clear 50% of the hamsters of the amebic infection.

The procedure for testing the compounds of the invention against *E. criceti* in the hamster is described as follows: Female hamsters naturally infected with *E. criceti* and ranging in weight from 95 to 145 g. are individually weighed and randomly sorted into groups of five animals; each group varies less than 10 g. from a designated weight for the group. To confirm presence of the infection, five hamsters are randomly selected from the weight ranges of 100, 120 and 140 g. groups and are killed. A portion of the cecum of each hamster is suspended in physiologically normal saline and examined microscopically (100×) for trophozoites of *E. criceti*. The compound being tested in suspended at the desired daily dose in 10% gelatin and orally administered via stomach tube to hamsters in subdivided doses twice daily approximately eight hours apart for three consecutive days. On the fourth day each of the test animals is killed and a cecal scraping examined as in the case of the infected control hamsters. When a preparation is determined to be free of amebae, a second specimen is taken from another part of the cecum of the same hamster and thoroughly examined before the hamster is declared to be cleared of trophozoites.

Whereas the 1-(halogenated-acetyl)-5-R-6-($Ac_2O$)-1,2,3,4-tetrahydroquinolines of formula I have been found to have high intestinal amebicidal activity at low dose levels when tested by the above-described procedure, the said prior art 1-acetyl-1,2,3,4-tetrahydro-6-quinolinol [Svensson et al., ibid.] when tested by the same procedure was found to be ineffective at a dose level as high as 100 mg./kg./day × 3 days (only one out of four hamsters was cleared of the amebic infection or the same as found for the non-medicated control animals). In contrast, 1-(chloroacetyl)-1,2,3,4-tetrahydro-6-quinolinol (Example A-8) cleared ten out of ten hamsters of the amebic infection at a dose level of 3.12 mg./kg./day × 3 days; 1-(dichloroacetyl)-1,2,3,4-tetrahydro-6-quinolinol (Example A-1) cleared five out of five hamsters of the amebic infection at 1.56 mg./kg./day × 3 days; 1-(dichloroacetyl)-6-(2-furoyloxy)-1,2,3,4-tetrahydroquinoline (Example A-2) cleared five out of five of the hamsters of the amebic infection at a dose level of 0.78 mg./kg./day × 3 days; 1-(dichloroacetyl)-1,2,3,4-tetrahydro-6-(2-thenoyloxy)quinoline (Example A-3) cleared five out of five of the hamsters of the amebic infection at a dose level of 0.20 mg./kg./day × 3 days; 6-benzoyloxy-1-(dichloroacetyl)-1,2,3,4-tetrahydroquinoline (Example A-4) cleared five out of five hamsters of the amebic infection at a dose level of 0.39 mg./kg./day × 3 days; and, 5-chloro-1-(dichloroacetyl)-1,2,3,4-tetrahydro-6-quinolinol (Example B-1) and 5-bromo-1-(dichloroacetyl)-1,2,3,4-tetrahydro-6-quinolinol (Example B-2) each cleared eight out of ten hamsters of the amebic infection at a dose level of 0.78 mg./kg./day × 3 days.

The actual determination of the numerical antiamebic data definitive for a particular compound of the invention is readily obtained according to the above-described standard test procedure by technicians versed in chemotherapeutic test procedures, without any need for any extensive experimentation.

The compounds of the invention can ordinarily be prepared for use by incorporating them in unit dosage form as tablets or capsules for oral administration either alone or in combination with suitable adjuvants such as sodium bicarbonate, starch, granulated sugar, lactose, dextrose, mannitol, talc, magnesium stearate, dibasic calcium phosphate, sodium lauryl sulfate, avicel, and the like.

I claim:
1. A compound of the formula

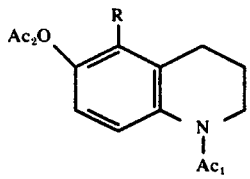

where $Ac_1$ is haloacetyl, dihaloacetyl or trihaloacetyl with halo being chloro or bromo, R is hydrogen, chloro or bromo, and $Ac_2$ is hydrogen, $Ac_1$, alkanoyl having from one to sixteen carbon atoms, benzoyl, 2(or 3)-thenoyl, 2(or 3)-furoyl or N-(lower-alkyl)carbamoyl.

2. A compound according to claim 1 where $Ac_1$ is dichloroacetyl.
3. A compound according to claim 2 where R is hydrogen.
4. A compound according to claim 2 where R is chloro.
5. 1-(Dichloroacetyl)-1,2,3,4-tetrahydro-6-quinolinol according to claim 3.
6. 5-Chloro-1-(dichloroacetyl)-1,2,3,4-tetrahydro-6-quinolinol according to claim 4.
7. 1-(Dichloroacetyl)-1,2,3,4-tetrahydro-6-(2-thenoyloxy)quinoline according to claim 3.
8. 5-Chloro-1-(dichloroacetyl)-1,2,3,4-tetrahydro-6-(2-thenoyloxy)quinoline according to claim 4.
9. 1-(Dichloroacetyl)-6-(2-furoyloxy)-1,2,3,4-tetrahydroquinoline according to claim 3.
10. 5-Chloro-1-(dichloroacetyl)-6-(2-furoyloxy)-1,2,3,4-tetrahydroquinoline according to claim 4.
11. 6-Benzoyloxy-1-(dichloroacetyl)-1,2,3,4-tetrahydroquinoline according to claim 3.

* * * * *